United States Patent [19]
Keenan

[11] Patent Number: 5,880,164
[45] Date of Patent: Mar. 9, 1999

[54] NICOTINE-FREE SMOKING MATERIAL

[75] Inventor: Robert M. Keenan, Baltimore, Md.

[73] Assignee: LecTec Corporation, Minnetonka, Minn.

[21] Appl. No.: 724,906

[22] Filed: Oct. 3, 1996

Related U.S. Application Data

[63] Continuation of Ser. No. 398,528, Mar. 6, 1995, abandoned.
[51] Int. Cl.[6] .............................. A24B 15/00; A61K 9/72; A61K 31/465
[52] U.S. Cl. .......................... 514/813; 131/270; 131/347; 131/359; 514/343; 514/958
[58] Field of Search ...................................... 131/270, 271, 131/272, 273, 347, 359; 514/343, 813, 958

[56] References Cited

U.S. PATENT DOCUMENTS

| | | | |
|---|---|---|---|
| 2,981,641 | 4/1961 | O'Neill | 131/17 |
| 3,048,520 | 8/1962 | McKennis, Jr. et al. | 514/343 |
| 3,821,960 | 7/1974 | Egri | 131/297 |
| 3,870,794 | 3/1975 | Hutchinson et al. | 514/343 |
| 4,038,993 | 8/1977 | Geiss et al. | 131/308 |
| 4,153,063 | 5/1979 | Roselius et al. | 113/297 |
| 4,289,147 | 9/1981 | Wildman et al. | 131/290 |
| 4,598,720 | 7/1986 | Gabriel | 131/335 |
| 4,621,074 | 11/1986 | Bourne | 514/12 |
| 4,657,032 | 4/1987 | Door et al. | 131/336 |
| 4,848,373 | 7/1989 | Lenkey | 131/297 |
| 5,643,928 | 7/1997 | Keenan | 514/343 |
| 5,747,512 | 5/1998 | Keenan et al. | 514/343 |
| 5,776,956 | 7/1998 | Rolf | 314/343 |

FOREIGN PATENT DOCUMENTS

| | | |
|---|---|---|
| 273715 | 8/1962 | Australia . |
| 1115369 | 5/1968 | United Kingdom . |
| 93/23045 | 11/1993 | WIPO . |

OTHER PUBLICATIONS

Jarvik et al. Pharmacological Treatent of Tobacco Dependence. Pharmacol–Biochem–Behav. vol. 30, No. 1, pp. 279–294. (May 1988).
Heatherton et al. The Fagerstrom Test for Nicotine Dependence: A Revision of the Fagerstrom Tolerance Questionaire. Br.–J–Addict., 86(9), pp. 1119–1127. (Sep. 1999).
Pomerleau et al. Reliability of the Fagerstrom Tolerance Questionaire and the Fagerstrom Test for Nicotine Dependence. Addict–behav. 19(1) pp. 33–39/ (Jan. 1994–Feb. 1994).
"American Psychiatric Assoc., Diagnostic and Statistical Manual of Mental Disorders",Washington, DC (3rd ed.), pp. 159–160, 176–178 (1980).
"Methyl Pyrrolidone Preparation Oxidatio Methyl Pyrrolidone Potassium Sodium Ferricyanide Aqueous Solution", *Database WPI, Derwent Publications Ltd.*, London, GB; AN 80–28065c, XP002005722 & JP,A,55 031 005 (Japan Tobacco & Salt Pub), (1988).
"The Health Consequences of Smoking: Nicotine Addiction. A Report to the Surgeon General", *US Gov't Print. Off.*, *Washington, DC, DHHS Publication No. (CDC) 88–8406 (1988)*, .
Beckett, A.H., et al., "A possible relationship between pKal and lipid solubility and the amounts secreted in urine to some tobacco alkaloids give to man", *J. Pharma. Pharmacol.*, 24, 115–120 (1972).

(List continued on next page.)

*Primary Examiner*—Robert H. Harrison
*Attorney, Agent, or Firm*—Schwegman, Lundberg, Woessner & Kluth P.A.

[57] ABSTRACT

A smoking material is provided that is useful to alleviate the symptoms of the tobacco withdrawal syndrome comprising an amount of continine or a pharmaceutical acceptable salt thereof in combination with a non-toxic vegetable material, which amount is effective to reduce or eliminate at least one of the symptoms of tobacco withdrawal syndrome in a human when the smoking material is smoked by a human.

7 Claims, 8 Drawing Sheets

MINNESOTA WITHDRAWAL SYMPTOM CHECKLIST

1. RATE THOSE SYMPTOMS WHICH YOU ARE EXPERIENCING RIGHT NOW.

|   | NONE | SLIGHT | MILD | MODERATE | SEVERE |
|---|---|---|---|---|---|
| A. CRAVING FOR CIGARETTES | 0 | 1 | 2 | 3 | 4 |
| B. IRRITABILITY/FRUSTRATION/ANGER | 0 | 1 | 2 | 3 | 4 |
| C. ANXIETY | 0 | 1 | 2 | 3 | 4 |
| D. DIFFICULTY CONCENTRATING | 0 | 1 | 2 | 3 | 4 |
| E. RESTLESSNESS | 0 | 1 | 2 | 3 | 4 |
| F. INCREASED APPETITE | 0 | 1 | 2 | 3 | 4 |
| G. DEPRESSED MOOD | 0 | 1 | 2 | 3 | 4 |
| H. IMPATIENCE | 0 | 1 | 2 | 3 | 4 |

OTHER PUBLICATIONS

Benowitz, N.L., et al., "Cotinine disposition and effects", *Clin Pharmacol. Ther.,* 34, 604–611 (Nov. 1983).

Bowman, E.R., et al., "Studies on metabolism of (–) –Continine in the Human", *J. Pharmacol. Exp. Ther.,* 135, 306–311 (1962).

Curvall, M., et al., "The pharmacokinetics of continine in plasma and saliva from non–smoking healthy volunteers", *Eur. J. Clin. Pharmacol.,* 38 281–287, (1990)

De Schepper, P.J., et al., "Kinetics of Cotinine after Oral and Intravenous Administration to man", *Eur. J. Clin. Pharmacol.,* 31, 583–588.

Gabrielsson, J., et al., "Constant–rate infusion of nicotine and cotinine. I. A physiological pharmacokinetic analysis of the cotinine disposition, and effects on clearance and distribution in the rat", *J. Pharmacokinetics Biopharmaceutics,* 15, 583–599 (1987).

Goldberg, S.R., et al., "Nictone and Some Related Compounds: Effects on Schedule–Controlled Behavior and Discriminative Properites in Rates", *Psychopharmacology,* 97, 295–302 (1989).

Hughes, J., et al., "Effects of Abstinence from Tobacco, A Critical Review", *Research Advances in Alcohol and Drug Problems, 10, Plenum Press, New York; Lynn Kolowski, ed;* 317–398 (1990).

Keenan, R.M., et al., "Reply to Mr. Foulds", *Clin. Pharmacol. Ther.,* 57, 95–97, (Jan., 1995).

Liberto, J.G., et al., "Cotinine in the Treatment of Cigarette Smoking", *J. Addictive Dis.,* 14, Abstract No. 11A, p. 147, (1995).

Mckennis, H., et al., "N–Methylation of Nicotine and Cotinine in Vivo", *J. Biol. Chem.,* 238, 719–723 (1963).

Risner, M.E., et al., "Effects of Nicotin, Cocaine and Some of their Metabolites on Schedule–Controlled Responding by Beagle Dogs and Squirrel Monkeys", *J. Pharmacol. Exp. Ther.,* 234, 113–119 (1985).

Scherer, G., et al., "Pharmacokinetics of Nicotone, Cotinine, and 3"– Hydroxzycotinine in Cigarette Smokers", *Klin. Wochenschr.,* 66 (Suppl XI), 5–11 (1988).

Takada, K., et al., "Discriminitive stimulus effects of intravenous 1–nicotine and nicotine analogs or metabolites on squirrel monkeys", *Psychopharmacology,* 99, 208–212 (1989).

Keenan, R.M., et al., "Pharmacodynamic Effects of Cotinine in Abstinent Cigarette Smokers", *Clin. Pharmacol. Ther.,* 55, 581–590, (May, 1994).

Yamamoto, K.I., et al., "Nicotine–Induced EEG and Behavioral Arousal", *Int. J. Neuropharmacol.,* 4, 359–373 91965).

FIG. 1

MINNESOTA WITHDRAWAL SYMPTOM CHECKLIST

1. RATE THOSE SYMPTOMS WHICH YOU ARE EXPERIENCING <u>RIGHT NOW</u>.

|   | NONE | SLIGHT | MILD | MODERATE | SEVERE |
|---|---|---|---|---|---|
| A. CRAVING FOR CIGARETTES | 0 | 1 | 2 | 3 | 4 |
| B. IRRITABILITY/FRUSTRATION/ANGER | 0 | 1 | 2 | 3 | 4 |
| C. ANXIETY | 0 | 1 | 2 | 3 | 4 |
| D. DIFFICULTY CONCENTRATING | 0 | 1 | 2 | 3 | 4 |
| E. RESTLESSNESS | 0 | 1 | 2 | 3 | 4 |
| F. INCREASED APPETITE | 0 | 1 | 2 | 3 | 4 |
| G. DEPRESSED MOOD | 0 | 1 | 2 | 3 | 4 |
| H. IMPATIENCE | 0 | 1 | 2 | 3 | 4 |

NICOTINE-FREE SMOKING MATERIAL

This is a continuation of application Ser. No. 08/398,528, filed Mar. 6, 1995, abandoned.

BACKGROUND OF THE INVENTION

Cigarette smoking continues to be the major preventable cause of death in the United States resulting in nearly 400,000 deaths per year due to cancer and heart disease. Despite the potential adverse health effects, grave consequences, the vast majority of cigarette smokers are unable to cease smoking.

The lack of smoking cessation success is thought to be related to the tobacco withdrawal syndrome or tobacco abstinence syndrome that most smoker experience during their attempts to quit. See, Office of Smoking and Health, *The Health Consequences of Smoking: Nicotine Addiction. A Report to the Surgeon General*, U.S. Govt. Print. Off., Washington, D.C., DHHS Pub. No. (CDC) 88–8406 (1988). The most common effects are similar to those in almost all abstinence syndromes, and include decreased heart rate, anxiety, difficulty concentrating, impatience, irritability and restlessness. See, American Psychiatric Assoc., *Diagnostic and Statistical Manual*, Washington D.C. (3rd ed. 1980) at pages 159–160, 176–178. Most withdrawal effects occur within 24 hours, peak in the first 1–2 weeks and significantly decrease at one month. It is widely believed that the effects of abstinence from tobacco are due to nicotine deprivation, and that abstinence effects from smoking prevent smokers from stopping. See, J. R. Hughes et al., in *Research and Advances in Alcohol and Drug Problems, Vol.,* 10, L. T. Kozlowski et al., eds., Plenum Pub. Corp. (1990) at pages 317–398.

Of the pharmacological approaches to aiding cessation of smoking, nicotine replacement, e.g., via transdermal nicotine patches or nicotine gum is the most widely used. Nicotine gum decreases abstinence discomfort, especially anxiety, decreased memory and irritability. On the other hand, nicotine gum does not reliably decrease weight gain or craving. Also, discontinuing use of nicotine gum leads to some of the same symptoms as the cigarette withdrawal syndrome. Furthermore, nicotine is toxic, and the availability of nicotine gum or patches poses a risk of poisoning to children and pets.

Other studies have demonstrated that alpha-2 agonists, such as clonidine, decrease postcessation anxiety, irritability and difficulty concentrating. Decreased sympathetic activity has been postulated to be the mechanism by which these drugs decrease abstinence effects. Although tobacco abstinence has some effects that could be attributed to sympathetic activity, it lacks the typical signs and symptoms of sympathetic overactivity, such as tachycardia, diaphoresis and hypertension. Thus, the mechanism by which alpha-2 agonists exert their effects is unclear. While a number of other pharmacological treatments, such as use of doxepin, ACTH, and corticotrophins, for abstinence symptoms have been tested, none of the studies reported baseline and postcessation values for abstinence symptoms. See, for example, S. J. Bourne (U.S. Pat. No. 4,621,074).

Therefore, a continuing need exists for pharmacological treatments that will facilitate smoking cessation, e.g., by blocking or relieving tobacco withdrawal syndrome, or reducing the symptoms of nicotine withdrawal.

SUMMARY OF THE INVENTION

The present invention provides a smoking material that comprises pharmacologically-effective amount of cotinine or a pharmaceutically-acceptable salt thereof. The amount of cotinine or the cotinine salt which is combined with the smoking material is preferably selected so that a human who smokes said material in a conventional manner, or who chews the material in the form of a "smokeless tobacco," will inhale or ingest an amount of cotinine that is effective to (a) alleviate at least one of the symptoms of the tobacco withdrawal syndrome (TWS), (b) alleviate the similar abstinence effects due to cessation of nicotine, or (c) decrease smoking behavior, i.e., tobacco consumption. Thus, a human subject attempting to remain abstinent from smoking, or to decrease smoking behavior, could smoke or chew the present smoking material to reduce his or her dependence on nicotine, or need to smoke or otherwise consume tobacco. The uncomfortable symptoms of TWS or of nicotine withdrawal can be effectively counteracted, while the subject receives the oral gratification of smoking. As discussed above, the symptoms of both tobacco and nicotine withdrawal are similar and are art recognized to include craving for nicotine, anxious/tense, irritable/angry, insomnia, impatience, restlessness, difficulty concentrating, increased eating, headache, excess hunger, somatic symptoms, weight gain and drowsiness.

In a preferred embodiment, the present invention also provides a therapeutic method to alleviate the craving for cigarettes, tobacco and/or nicotine that is associated with cessation of tobacco or nicotine use, e.g., by chewing or smoking, by the administration by smoking of an effective amount of cotinine or a pharmaceutically acceptable salt thereof, to a human in need of such treatment. However, the present invention is also useful to treat the symptoms of nicotine withdrawal which are due, for example, to cessation of use of nicotine gum or a nicotine transdermal patch. The present method is effective both to alleviate the TWS acutely and to permit patients to maintain abstinence from nicotine for extended periods of time. The present method is also effective to decrease smoking behavior.

The therapeutic administration of cotinine to abstinent smokers to relieve the symptoms of TWS has been disclosed in commonly-assigned U.S. patent application Ser. No. 07/885,315, filed May 18, 1992, as well as in commonly-assigned U.S. patent application Ser. No. 08/293,585, filed Aug. 22, 1994, in which (−)-cotinine base was orally administered to abstinent cigarette smokers in a double-blind placebo controlled study. The results of this study demonstrate that: (1) cotinine fumarate up to at least 160 mg is safe, (2) cotinine fumarate at the 80 mg dose suppresses specific withdrawal symptoms, and (3) at the 40 and 80 mg dose, cotinine fumarate suppresses total withdrawal discomfort. These effects occur at doses of cotinine which do not cause significant effects on heart rate and blood pressure.

Cotinine has many qualities which can enhance its value as a smoking cessation aid. Cotinine has a long in vivo half-life, complete oral bioavailability, minimal effect on the cardiovascular system, and has not been reported to be harmful even at very high doses in many species including man. Also, because cotinine has no significant effect on the heart, a combined pharmacologic treatment approach using cotinine and nicotine may be possible, as by the application of cotinine to low-nicotine tobacco.

The present invention also provides an article of manufacture comprising packaging material, such as a box or envelope and the like; a smoking material contained within said packaging material, wherein said smoking material comprises cotinine or a pharmaceutically acceptable salt thereof in an amount effective to alleviate the tobacco withdrawal syndrome or the symptoms of nicotine withdrawal, and wherein said packaging material includes instruction means which indicate that said cotinine or said pharmacologically acceptable salt thereof can be used for alleviating tobacco withdrawal syndrome, or the symptoms of nicotine withdrawal. Suitable instruction means include printed labels, printed package inserts, tags, and the like. Preferably, the smoking material is contained within a cigarette, cigar or is a shaped unit of a chewable vegetable material, such as a "chewing tobacco." As noted above, the smoking material is preferably nicotine-free.

DETAILED DESCRIPTION OF THE INVENTION

Cotinine

Cotinine (1-methyl-5-(3-pyridinyl)-2-pyrrolidinone) has the formula shown below:

The physiologically active form is the (−)-isomer, so as used herein, the term "cotinine" includes (−)-cotinine, or the racemic form, (±)-cotinine. The free base, depicted above, can be employed in the practice of the invention, as can the pharmaceutically acceptable salts. These include the amine-acid addition salts of nontoxic organic acids or inorganic acids, such as the tartarate, fumarate ("scotine"), citrate, maleate, malate, hydrobromide, hydrochloride, sulfate, phosphate and the like. For example, see F. Vaitekunas, *J. Amer. Chem. Soc.*, 79, 149 (1957). E. R. Bowman et al., in *J. Pharmacol. and Exp. Ther.*, 135, 306 (1962) report the preparation of (−)-cotinine free base from (−)-nicotine. The preparation and purification of (−)-cotinine fumarate is described by N. L. Benowitz et al., *Clin. Pharmacol. Ther.*, 34, 604 (1983).

Cotinine is the major metabolite of nicotine which accumulates in the body as a result of nicotine exposure and has previously been believed to be pharmacologically inactive. For example, see N. L. Benowitz, "The use of biologic fluid samples in assessing tobacco smoke consumption", in *Measurement in the Analysis and Treatment of Smoking Behavior*, J. Grabowski et al., eds., NIDA Research Monograph No. 48, U.S. DHHS. PHS. ADAMHA (1983). In contrast to nicotine, cotinine has a relatively long terminal elimination half-life (two versus sixteen hours, respectively). Due to this pharmacological characteristic, cotinine has become the principally used objective biochemical marker of nicotine exposure in cigarette smoking and/or cessation-related research paradigms.

While cotinine is a well-known metabolite of nicotine and is routinely measured in many laboratories, no systematic investigation of the physiological and subjective effects produced by intravenous cotinine administration has been performed in humans. K. I. Yamamoto et al., *International J. Neurophamacol.*, 4, 359 (1965) reported that intravenous cotinine produced increases only slightly in EEG activity and behavioral arousal in cats with only a slight decrease in blood pressure. In squirrel monkeys, intramuscular cotinine injections increased rates of responding on fixed interval schedules of reinforcement over a wide range of doses (M. E. Risner et al., *J. Pharmacol. and Exp. Ther.*, 234, 113 (1985); S. R. Goldberg et al., *Psychopharmacology*, 27, 295 (1989)). Hutchinson et al. (U.S. Pat. No. 3,870,794), without supporting data, disclose that cotinine can be therapeutically administered to treat certain emotional disorders such as to reduce anger, hostility, irritability, frustration, fear, anxiety and nervousness. These findings, taken together, suggest that cotinine is behaviorally active. However, the pharmacologic mechanism of action has yet to be determined.

In two recent human studies, the pharmacokinetic profiles of intravenous and orally administered cotinine were examined without emphasis on measuring the subjective and/or physiological changes induced by this compound (N. L. Benowitz et al., *Clin. Pharmacol. and Therapeutics*, 34, 604 (1983); P. J. DeSchepper et al., *Eur. J. Pharmacol.*, 31, 583 (1987)). Moreover, using an uncontrolled experimental design, Benowitz et al., *Clin. Pharm. and Ther.*, 34, 604 (1988), found that intravenous cotinine infusion over 60 min. produced no cardiovascular changes and significant decreases in subjective ratings of desire to smoke, irritability, low energy and anxiety/tension. These changes were comparable to placebo-induced changes found in other experiments with nicotine. Using a rapid infusion of cotinine over 5 minutes, no significant changes in the subjective ratings were observed. Consequently, Benowitz and his colleagues concluded that cotinine lacked significant pharmacologic activity in humans.

In contrast to these studies, the present invention is based on the ability of cotinine to be self-administered in pharmacologically-effective amounts by inhalation of thermally-vaporized cotinine, as by smoking. Smoking is generally defined as the act of inhaling the fumes of burning plant material, and pre-treatment of the plant material to coat or impregnate it with cotinine can result in the delivery of a therapeutically-effective amount of cotinine to the user. Examples of smoking material effective as a carrier for the cotinine include nicotine-free tobacco, THC-free hemp, spices such oregano, sassafras, sage, spice-bush, clove and the like, grains, bark, leaves, cellulose, wood pulp, paper, and mixtures thereof. Other adjuvants conventionally employed in tobacco or tobacco substitutes can also be added, including binders, aroma modifiers, sweeteners, flavorings and fillers. These include minor but effective amounts of glycerol, citric acid, sugars, malic acid, fruit juice, honey, vanilla extract, cinnamon, anise, cloves, cellulose derivatives, calcium carbonate, nitrate zeolite salts, and the like. For example, patents which disclose modified tobacco or vegetable-based non-tobacco smoking materials include U.S. Pat. Nos. 4,296,762, 4,233,993, 3,820,548, 3,747,607, 3,638,160, 3,424,171, 3,369,552, 3,323,524 and 3,112,754.

The smoking material is preferably coated or impregnated with cotinine or a volatile salt thereof, for example, by infusing it or by spraying an aqueous solution or alcoholic solution of the cotinine salt onto the smoking material and drying it, either before or after macerating or shredding it for shaping or packaging.

Cotinine or the cotinine salt can be provided to the extent of about 5–50 mg of cotinine or cotinine salt per gram of smoking materials (0.5–5 wt-% of cotinine). The smoking material is then smoked in a pipe by the user (about 5–20 g treated smoking material), or is formed into cigarettes (about 0.75–1.25 g), or cigars (about 5–20 g). At these loads of treated smoking material, the smoker would self-administer about 1–20 mg cotinine per gram of smoking material which is consumed. For example, a smoker who smokes 20 cigarettes per day would ingest about 100 mg-1.0 g of cotinine, resulting in an actual bioavailable dose of about 20–400 mg of cotinine.

Therefore, a cotinine-treated cigarette, cigar, unit of smoking material and the like can be considered a pharmaceutical unit dosage form, effective to deliver a preselected amount of cotinine to the user. Likewise, a pack of cotinine-treated cigarettes, a box or package of cotinine-treated cigars, a tin or soft pack of tobacco treated with cotinine, and the like, are "kits" as broadly defined herein, insofar as they also comprise instruction means related to the self-administration of cotinine therefrom in accord with the present method.

The invention will be further described by reference to the following detailed Example.

Example I
Oral Administration of (−)-Cotinine Fumarate

To investigate the effects of oral cotinine on the symptoms of the tobacco withdrawal syndrome (TWS) as experienced by abstinent smokers, under controlled conditions, the following double blind, placebo controlled study was conducted at the University of Minnesota. More specifically, the study was conducted to (1) determine the safety of various doses of cotinine fumarate; (2) determine blood cotinine concentrations attained from various doses of cotinine fumarate; and (3) determine effects of various doses of cotinine fumarate on withdrawal signs and symptoms including physiological and subjective symptoms. The results of this study demonstrate the: (1) cotinine fumarate up to 160 mg is safe, (2) cotinine fumarate at the 80 mg dose suppresses specific withdrawal symptoms, and (3) at the 40 and 80 mg dose, cotinine fumarate suppresses total withdrawal discomfort. These effects occur at doses of cotinine which do not cause effects on heart rate and blood pressure.

Methods

A. Subjects: Subjects (N=37 male and female smokers) were recruited from the Minneapolis/St. Paul metropolitan area via newspaper advertisements. Subjects were initially screened over the telephone. If they met the telephone screening criteria, then they were seen by the research coordinator and physician. At this screening session, informed consent was obtained. Subjects were required to complete a smoking history and Fagerstrom Nicotine Tolerance Questionnaire. In addition, an alveolar carbon monoxide sample and blood samples to measure cotinine and nicotine levels were obtained. The physician then obtained a medical and concomitant medication history and conducted a physical examination that included a 12-lead electrocardiogram (ECG) and laboratory screening of blood and urine specimens. Subjects were included if they: (a) smoked at least one pack of cigarettes/day for at least one year; (b) submitted a CO<10 ppm; and (c) were in good health (e.g., no history of myocardial infarction, angina pectoris, sustained or episodic cardia arrhythmias, symptomatic peripheral vascular disease) as verified by medical history, screening examination, and screening laboratory tests. Subjects were excluded if they: (a) required any form of regular psychotropic medication; (b) chronically used systemic steroids or antihistamines; (c) abused alcohol or any other recreational or prescription drug; (d) used any other tobacco products including smokeless tobacco. To maximize compliance and completion of the study, subjects were paid $700 for their participation.

B. Procedure: This study used a between-subject design with one of the doses of cotinine or placebo as the across subject variable. The study was run at the University of Minnesota General Clinical Research Center, Minneapolis, Minn. U.S.A., a federally funded inpatient research ward. Total participation in this study was 10 days. See Table 1 for experimental procedures.

TABLE 1

Experimental Procedure

| Cue Exposure | | Cue Exposure | | | Cue Exposure | | | | |
|---|---|---|---|---|---|---|---|---|---|
| 1 | 2 | 3 | 4 | 5 | 6 | 7 | 8 | 9 | 10 |
| Ad Lib | | Placebo | | Cotinine | | | Placebo | | Discharge |

Subjects were admitted to research ward at noon. During the first two days of the study, baseline measure were obtained while the subject smoked cigarettes on an ad libitum basis. Subjects were required to be abstinent from cigarettes beginning in the morning of the third day. All subjects were given placebo at this time to allow some clearance of nicotine. On the morning of the fourth day, subjects were given placebo or one of the following oral doses of cotinine fumarate: 40 mg, 80 mg, and 160 mg. Nine subjects were to be run per each condition. Doses of cotinine were tested in ascending order. The subjects who are assigned to placebo were interspersed across the active dose conditions so that the blind would be maintained. If no adverse effects were detected for a particular dose, then the next higher dose was tested with the next group of subjects. Subjects were given one of the oral doses of cotinine fumarate/placebo for the next 3 days. Three days of cotinine dosing were chosen since the maximum tobacco withdrawal effects are observed during 24–72 hours of abstinence. See Hughes et al., Res. Adv. in Alcohol & Drug Problems, 10, Kozlowski et al., eds., Plenum Pub. (1990) at pages 317–398. Beginning on the eighth day, all subjects were; required to take placebo again for three more days. This placebo condition would allow observation of withdrawal signs and symptoms from cotinine fumarate. To minimize experimenter bias, the investigators and nurses involved with assessment, however, were led to believe that subject during this placebo phase were randomly assigned to continue to take the medication given to them prior three days or assigned to placebo. Subjects were discharged in the morning of the tenth day if medical and psychological status were considered normal.

Abstinence was confirmed by biochemical verification (e.g., alveolar carbon monoxide) obtained at random times three times/day, evenly distributed across the day. Weight (after voiding) in the hospital gown was recorded and a sleep scale completed every morning. See Table 2.

TABLE 2

NICOTINE METABOLITE STUDY - TEST CHECKLIST

| TEST | DAYS TESTED | 0630 | 0830 | 0930 | 1000 | 1200 | 1500 | 1800 | 2100 |
|---|---|---|---|---|---|---|---|---|---|
| PHYSICAL TESTING | | | | | | | | | |
| WEIGHT | PE, D0–10 | X | | | | | | | |
| BLOOD PRESSURE | PE, D0–10 | | X | X | X | X | X | X | X |
| HEARTRATE | PE, D0–10 | | X | X | X | X | X | X | X |
| SKIN TEMPERATURE | DAY 1–9 | | X | | X | X | X | | |
| EKG | PE, D1–9 | | X | | | X | | | |
| PSYCH TESTING | | | | | | | | | |
| MWSC- MN.W/DRAWAL SX. CHECKLIST | DAY 1–9 | | X | | X | X | X | | |
| POMS | DAY 1–9 | | X | | X | X | X | | |
| VISUAL ANALOG SCALE | DAY 1–9 | | X | | X | X | X | | |
| VISUAL ANALOG SCALE- DRUG EFFECTS | DAY 3–9 | | X | | X | X | X | | |
| ADDICTION RESEARCH CENTER INVENTORY | DAY 1–9 | | X | | X | X | X | | |
| ADVERSE EFFECTS | DAY 1–9 | | X | | X | X | X | | |
| QUESTIONNAIRE OF SMOKING URGES | DAY 1–9 | | X | | X | X | X | | |
| RECORD OF OBSERVED W/DRAWAL SX'S | DAY 1–9 | | X | | X | X | X | | |
| SLEEP DIARY | DAY 1–10 | | X | | | | | | |

Figure 1:
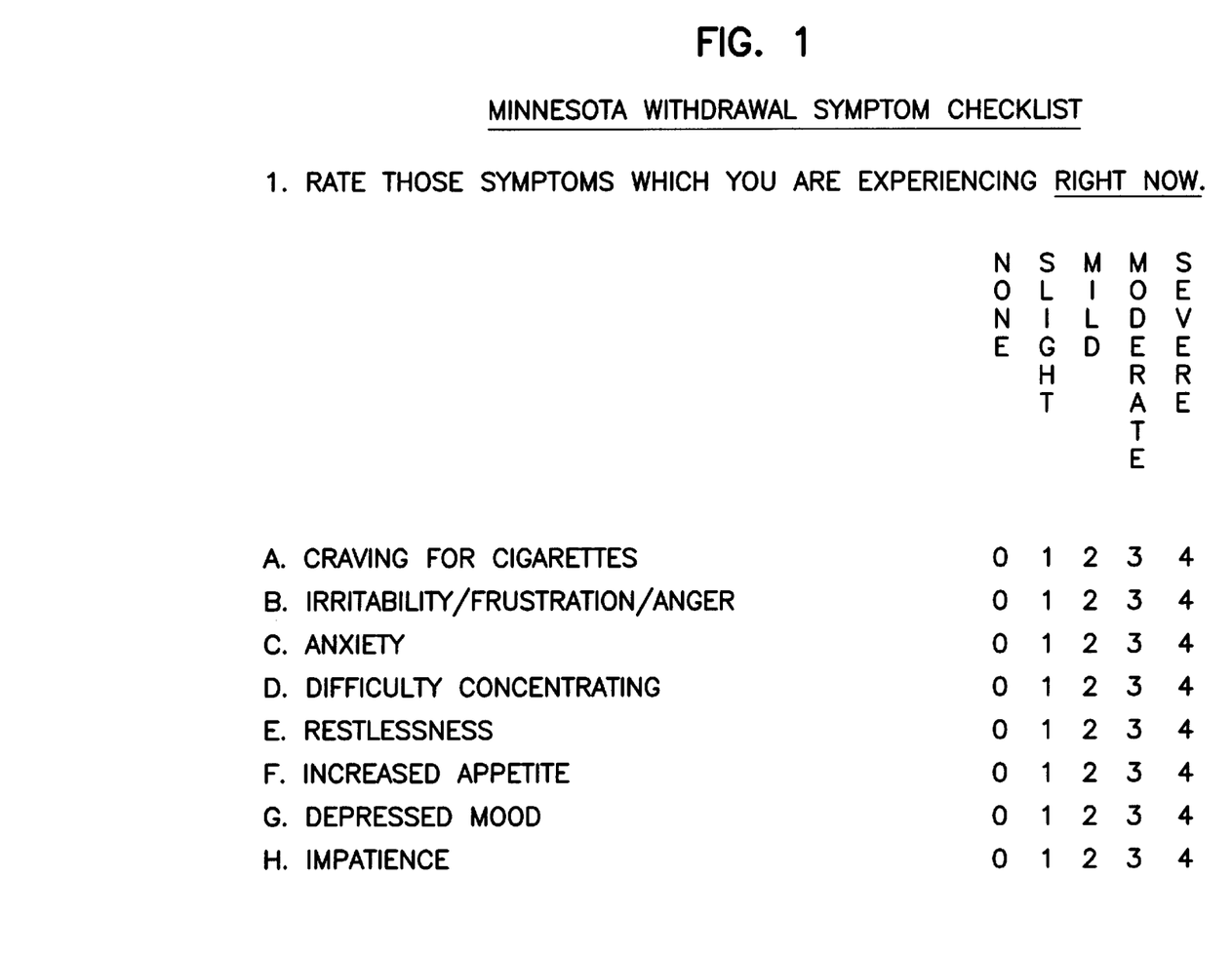
FIG. 1 depicts the Minnesota Withdrawal Symptom Checklist.

Subjects were required to complete subjective measures at the same times in the morning and afternoon throughout the study. See Table 2. These measures included the Addiction Research Center Inventory (Martin, Sloan, Sapira and Jasinski, Clin. Pharmacol Ther., 1, 245 (1971)) which measures drug-like effects; the Profile of Mood States (McNair et al., Manual Profile of Mood States, San Diego Educational and Industrial Testing Service (1971)) which measures various moods such as depression-dejection, tension-anxiety, confusion, anger-hostility, vigor and fatigue; a VAS (which measures nicotine-like effects as well as how much an individual likes cotinine); the modified Minnesota Withdrawal Symptom Checklist (see FIG. 1; Hughes and Hatsukami, Arch. of Gen. Psychol, 43, 289 (1986)) comprised symptoms of nicotine withdrawal as described in the DMS-IV (APA, 1994) which subjects rated on a 0 to 4 scale with 0=none, 1=slight, 2=mild, 3=moderate, 4=severe; and the Smoking Urges Questionnaire (Tiffany & Drobes, Brit. J. Addiction, 86, 1467 (1991)) which measured two factors, one reflecting intention, desire and anticipation to smoke, and the other factor reflecting anticipation of relief from negative affect, nicotine withdrawal and urgent or overwhelming desire to smoke.

Subjects were also measured at these times for vitals (sitting and standing blood pressure and heart rate), skin temperature, respiratory rate, assessed for adverse events, and a 12-lead EKG was obtained. Caloric intake was carefully monitored throughout the study. Meals, similar to ones normally ingested by the subjects, were planned by the registered dietician who then supervised the careful measurement and preparation of all the foods eaten by the subjects. Meal and snack trays (foods of various macronutrients made available to the subjects all day) were returned to the kitchen where all uneaten food and beverages were remeasured after each meal, thereby all the eaten food was recorded by type and amount. Food content was later analyzed and calculated for daily amount of carbohydrate, protein, fat, and calories. Caffeine intake was controlled and maintained at the same level throughout the study. The amount of caffeine intake allowed for each individual was based on the levels of intake prior to the study. Alcohol intake was prohibited. Serum nicotine/cotinine samples were obtained at noon throughout the study. On days 2 and 6, blood samples were obtained to measure corticosteroids. On days 7 and 10, routine lab tests were taken. An internist monitored the subjects for a period of 30 minutes after the subjects took the medication to assess for any signs of toxicity.

Subjects were exposed to smoking related cues on Days 2, 5 and 9 since tobacco withdrawal symptoms may be minimized in an inpatient hospital setting when all normal cues for smoking are minimal. This cue involved exposure to their own brand of cigarettes and ashtray. Subjects were asked to look at their cigarettes, ashtray and matches for 15 seconds, light their cigarettes for 5 seconds, observe their lit cigarettes for another 15 seconds, then extinguish their cigarettes. During the study, subjects are free to engage in activities provided by the unit. Their exposure to smoking related stimuli were minimized during these activities in order to maintain consistency in cue exposures across subjects.

(S)-Cotinine was synthesized and converted into its fumarate salt by the method of McKennis and Bowman, Biochemical Preparation, 1963, 10, 36 (1963). The crystalline material was purified and found to be greater than 98% pure with no nicotine contamination. This material was characterized by elemental analysis, proton and carbon NMR, gas chromatography, and DSC. The drug substance was formulated into capsule dosage form at the Research Pharmacy at the University of Minnesota. The doses prepared were placebo (0 mg) and 40 mg, 80 mg, and 160 mg of cotinine fumarate. These were tested for uniformity of content, stability and drug release rate by standard USP dissolution testing. The doses were coded to assure a double blind clinical experiment and provided to the research staff as needed.

Statistical Analysis

For purposes of this paper, only results on selective withdrawal measures will be reported. Demographic and smoking history variables were analyzed using oneway analysis of variance for continuous measures and chi square tests for categorical measures. When the between groups analysis of variance indicated a significant difference, multiple comparisons between treatment groups were performed using Tukey's HSD to determine which of the groups were significantly different from each other.

For the total withdrawal symptom score, a reliability analysis of the scale using Cronbach's alpha indicated that the craving and increased appetite items were not highly correlated with the other items on the scale. Consequently, these items were eliminated in the computation of the total withdrawal symptom score to increase the internal consistency of the scale.

The primary statistical analysis for the present study was performed using unbalanced repeated measure analysis. A between groups analysis comparing differences in withdrawal by treatment condition was conducted for all available subjects. Due to baseline differences between groups, cotinine level and number of cigarettes smoked daily were used as covariates in the analysis. Likelihood radio tests and Wald tests were used to determine the significance of each term in the model.

A. Effect of Cotinine on cigarette withdrawal. A repeated measures analysis was performed for the three days the subject was on medication. In addition to cotinine level and number of cigarettes smoked daily, the average score of the two baseline smoking days was used as covariate. For continuous measures, terms included in the regression model were an intercept, the three covariates, main effects for time of day, day on medication, medication dosage, and interaction of day on medication by medication dosage. For categorical measures, terms included in the logit or probit model were an intercept, the three covariates, main effects for time of day, medication dosage and day on medication.

Results

A. Demographics, smoking history and cotinine levels. Thirty-seven subjects entered the study and 35 subjects completed the study. Two of the subjects were discharged prior to assignment to the medication. One subject experienced family problems while on the unit, and the other experienced a reoccurrence of an ulcer. Nine subjects completed the protocol in each group except the 160 mg group, in which 8 subjects completed the study. The demographic and smoking history variables are shown in Table 3.

TABLE 3

| Variable | Placebo | 40 mg | 80 mg | 160 mg | P value |
|---|---|---|---|---|---|
| Females | 55.6 | 55.6 | 55.6 | 50.0 | |
| Age | 27.3 | 26.6 | 30.9 | 33.8 | .05 |
| Number of Cigarettes | 23.0 | 26.6 | 28.3 | 33.8 | .02 |
| Years of Smoking | 11.4 | 11.0 | 15.4 | 20.3 | .02 |
| Fagerstrom Score | 5.3 | 6.6 | 6.2 | 6.9 | .04 |
| Serum Cotinine | 228.4 | 288.1 | 263.9 | 350.2 | .00 |

Figure 2:
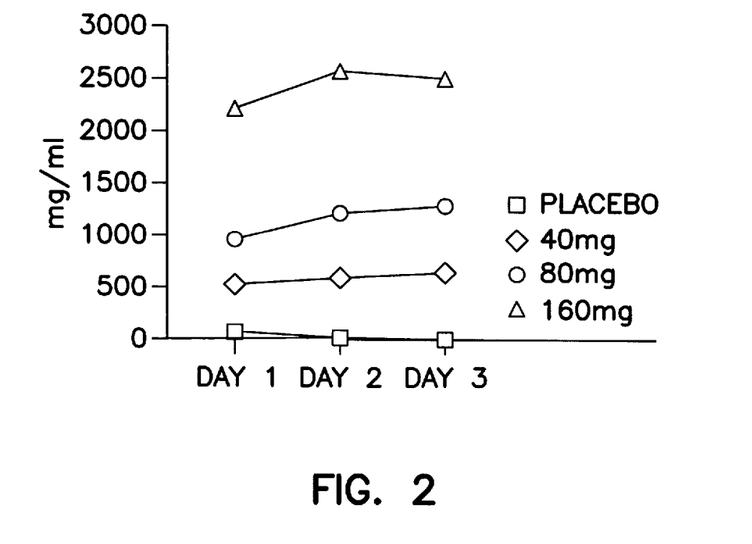
FIG. 2 is a graph depicting mean blood cotinine levels of the test subjects.
Figure 3:
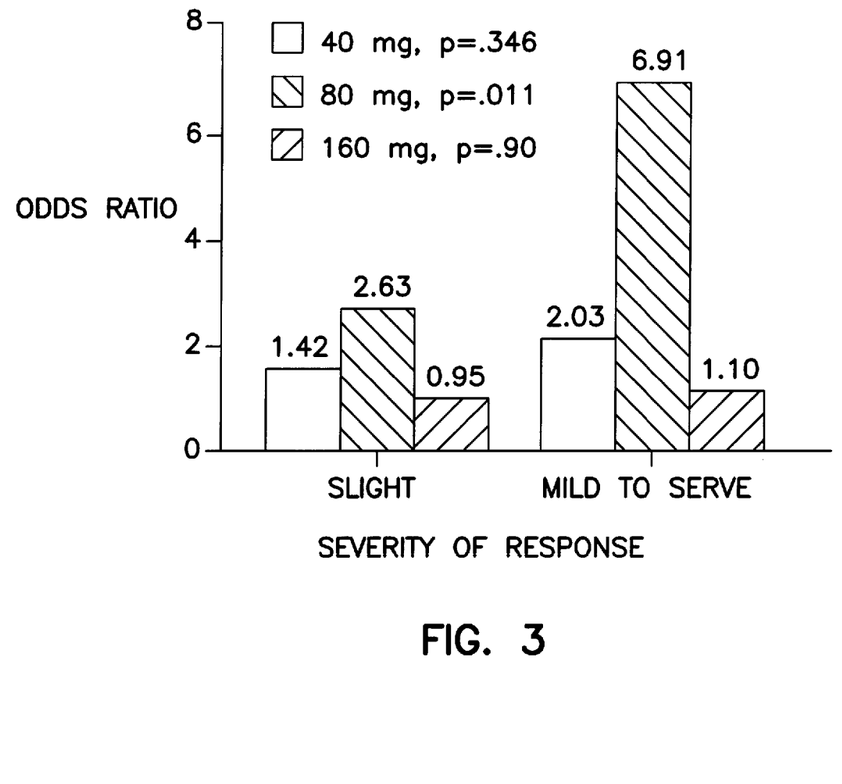
FIG. 3 is a graph depicting the odds ratio of no irritability to severity by dosage.
Figure 4:
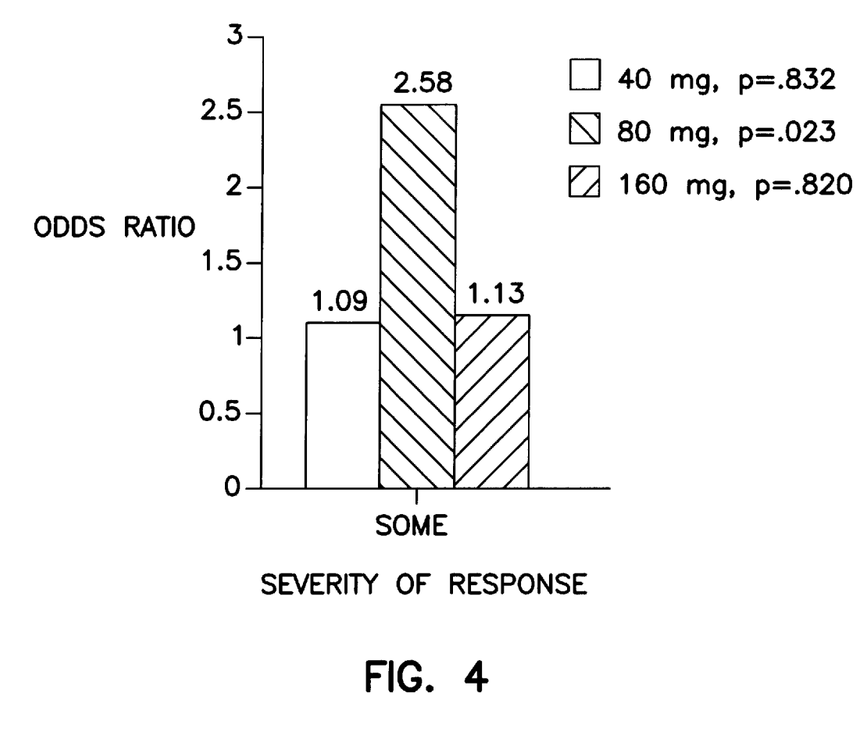
FIG. 4 is a graph depicting the odds ratio of no anxiety to some anxiety by dosage.
Figure 5:
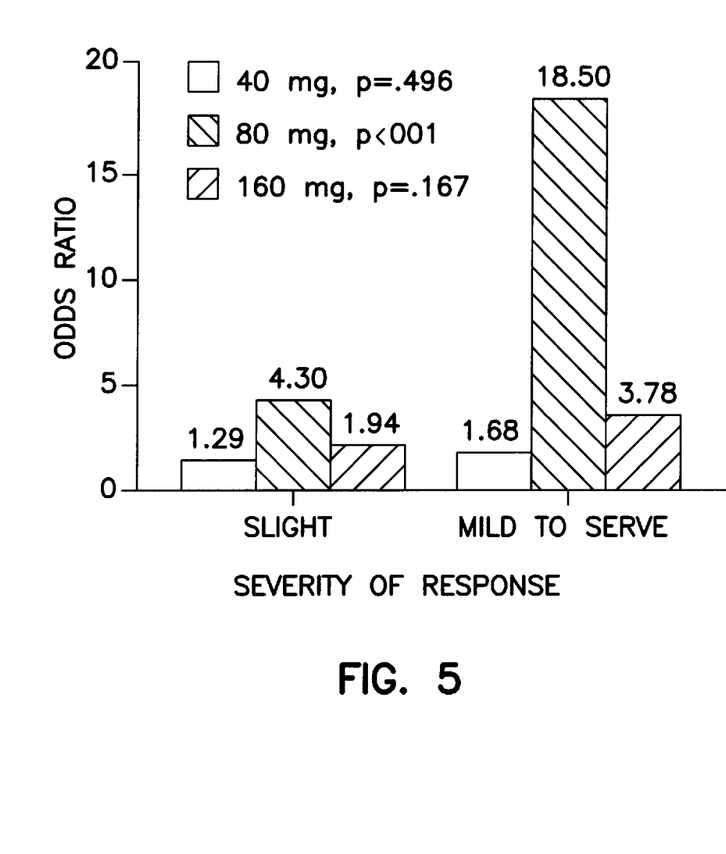
FIG. 5 is a graph depicting the odds ratio of no difficulty concentrating to level experienced.
Figure 6:
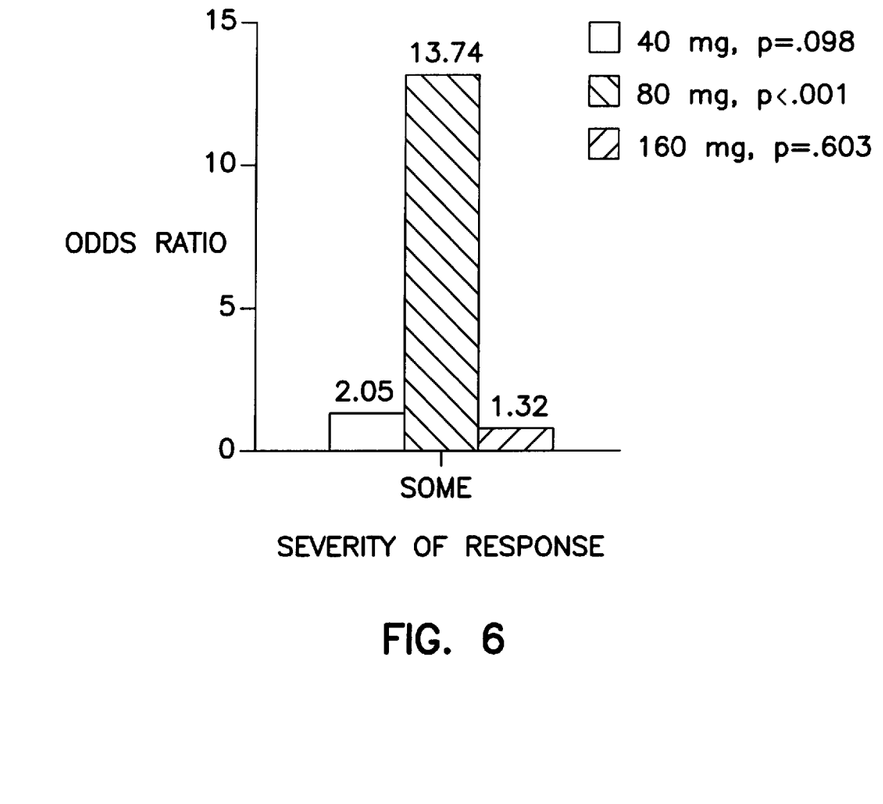
FIG. 6 is a graph depicting odds of experiencing no impatience to some impatience.
Figure 7:
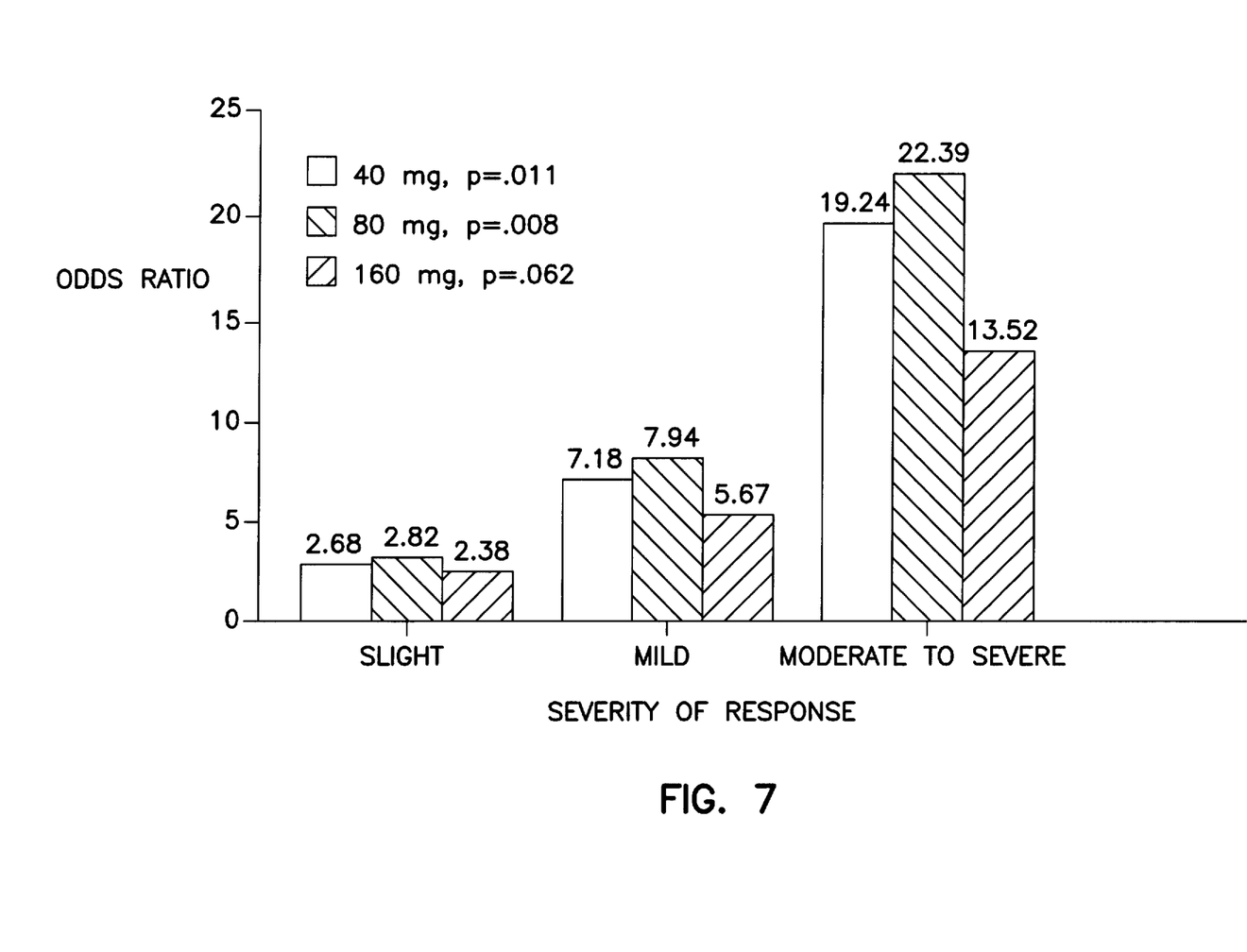
FIG. 7 is a graph depicting odds ratio of no increased appetite to level experienced.

Significant differences were observed in age, number of cigarettes, years of smoking, Fagerstrom Tolerance Questionnaire Score, and serum cotinine. Post hoc analyses showed significant differences between the 160 mg and placebo groups. Due to these differences among groups, cotinine level in mg/ml serum (shown in previous studies to be correlated with nicotine withdrawal symptoms) and number of cigarettes (which showed significant correlations with the other variables showing significant differences between treatment groups) were used as covariates. FIG. 2 shows the mean cotinine level attained for each of the three days on the medication. Significant differences were observed across the doses of cotinine ($p < 0.001$).

B. Safety of cotinine. No adverse effects were noted by the subjects that would warrant termination from the study. Ten subjects, however, experienced elevated liver function tests with 4 of these subjects in the placebo group, 1 subject in the 40 mg group, 3 subjects in the 80 mg group, and 2 subjects in the 160 mg group. Two subjects (one in the 40 mg and 80 mg group) were considered to have clinically insignificant elevations. For the 6 out of 8 subjects who complied with the follow-up visit(s) to obtain repeat liver function tests, the levels had decreased to normal.

C. Effect of cotinine on cigarette withdrawal symptoms.

1. Subjective effects:

FIGS. 3–7 show the cigarette withdrawal symptoms that showed significant differences across groups. For irritability/frustration/anger (FIG. 3), anxiety (FIG. 4), difficulty concentrating (FIG. 5) and impatience (FIG. 6), the 80 mg dose group scored experienced significantly less severe symptoms than the placebo group. For irritability, the odds were 2.6 times greater to experience no irritability than slight irritability, and 6.9 times greater to experience no irritability than mild to severe irritability. For anxiety, the odds were 2.6 times greater to experience no anxiety than any anxiety. For difficulty concentrating, the odds were 4.3 times greater in experiencing no difficulty than to experience slight difficulty in concentrating and 18.5 times greater in experiencing no difficulty concentrating than to experience mild to severe difficulty concentrating. For impatience, the odds were 13.7 times greater to experience no impatience than to experience any impatience.

Figure 8:
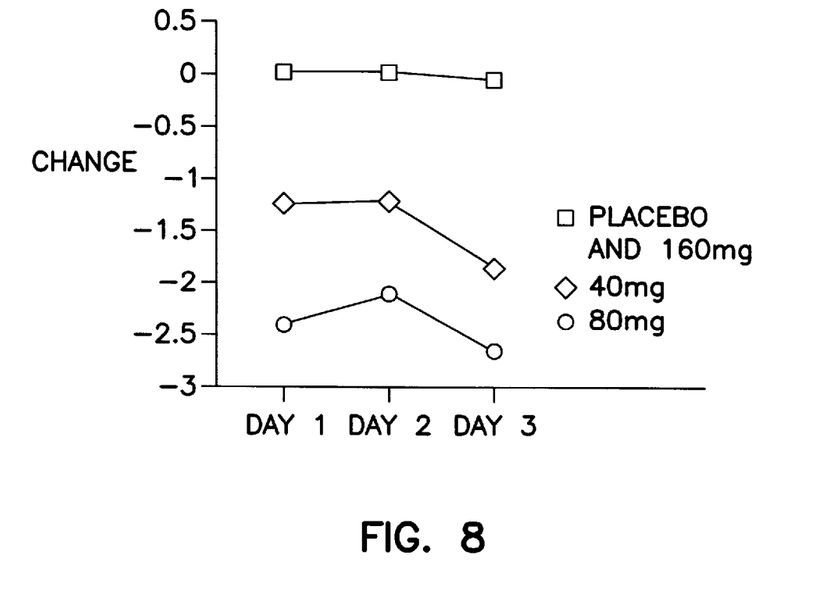
FIG. 8 is a graph depicting the change in the total withdrawal symptom score.

For increased appetite (FIG. 7) and total withdrawal score (FIG. 8), the 40 and 80 mg groups experienced significantly lower scores than placebo. For increased appetite, in the 40 mg condition, the odds were 2.7, 7.2 and 19.2 times greater in reporting no increased appetite than to have experienced slight, mild or moderate to severe increases in appetite, respectively. In the 80 mg condition, the odds were 2.8, 7.9, and 22.4 times greater in experiencing no increased appetite than to have experienced slight, mild or moderate to severe increase in appetite, respectively. The results for the total withdrawal score showed that there was a significant dose effect ($p < 0.007$), with the 40 mg ($p = 0.012$) and 80 mg ($p < 0.001$) dose groups reported experiencing significantly lower composite withdrawal syndromes than placebo. No significant differences were observed across doses for cradling, restlessness and depressed mood, or for the two main factors measured by the Smoking Urges Questionnaires. No significant differences were observed for caloric intake and specific macro nutrients.

2. Physiological effects:

No significant effects of cotinine were observed for any of the physiological measures (heart rate, systolic and diastolic blood pressure).

3. Effects of cotinine during cue exposure:

No significant effects of cotinine were observed for any of the physiological heart rate, systolic and diabolic blood pressure) and subjective withdrawal measures assessed during cue exposure conditions.

All publications and patents are herein incorporated by reference to the same extent as if each individual publication or patent was specifically and individually indicated to be incorporated by reference.

What is claimed is:

1. A method comprising administering to a human an effective amount of cotinine or a pharmaceutically acceptable salt thereof by smoking a non-toxic vegetable material coated or impregnated with cotinine, which amount is effective to assist in smoking cessation or to maintain abstinence from tobacco use by said human.

2. The method of claim 1 wherein the cotinine is (−)-cotinine.

3. The method of claim 2 wherein the cotinine is a salt of (−)-cotinine.

4. The method of claim 4 wherein the vegetable material is nicotine-free tobacco.

5. The method of claim 1 wherein the vegetable material comprises about 5–50 mg of cotinine per gram of vegetable material.

6. The method of claim 1 wherein a cigarette is smoked.

7. The method of claim 1 wherein a cigar is smoked.

* * * * *

UNITED STATES PATENT AND TRADEMARK OFFICE
CERTIFICATE OF CORRECTION

PATENT NO. : 5,880,164

DATED : Mar. 9, 1999

INVENTOR(S) : Robert M. Keenan

It is certified that error appears in the above-identified patent and that said Letters Patent is hereby corrected as shown below:

At Col. 11, line 5, please delete "4" following "claim" and insert --1--.

At the Abstract, line 3, please delete "continine" following "of" and insert --cotinine--.

At the Abstract, line 3, please delete "pharmaceutical" following "a" and insert --pharmaceutically--.

Signed and Sealed this

Seventh Day of December, 1999

Attest:

Q. TODD DICKINSON

Attesting Officer

Acting Commissioner of Patents and Trademarks